(12) United States Patent
Konkle et al.

(10) Patent No.: US 11,294,079 B2
(45) Date of Patent: Apr. 5, 2022

(54) METHODS AND SYSTEMS FOR A LAYERED IMAGING DETECTOR

(71) Applicant: GE Precision Healthcare LLC, Milwaukee, WI (US)

(72) Inventors: Nicholas Konkle, Sussex, WI (US); Daniel Lochner, West Allis, WI (US); Grant Schueneman, Waukesha, WI (US); Jahir Drago, Sussex, WI (US)

(73) Assignee: GE Precision Healthcare LLC, Milwaukee, WI (US)

( * ) Notice: Subject to any disclaimer, the term of this patent is extended or adjusted under 35 U.S.C. 154(b) by 291 days.

(21) Appl. No.: 16/719,294

(22) Filed: Dec. 18, 2019

(65) Prior Publication Data

US 2021/0190977 A1    Jun. 24, 2021

(51) Int. Cl.
    *G01T 1/24*     (2006.01)
    *A61B 6/00*     (2006.01)
    *A61B 6/03*     (2006.01)
    *G01N 23/046*   (2018.01)

(52) U.S. Cl.
    CPC .............. *G01T 1/244* (2013.01); *A61B 6/032* (2013.01); *A61B 6/4208* (2013.01); *G01N 23/046* (2013.01); *G01T 1/242* (2013.01)

(58) Field of Classification Search
    CPC ......... G01T 1/244; G01T 1/242; G01T 1/243; A61B 6/032; A61B 6/4208; A61B 6/4014; A61B 6/035; A61B 6/107; A61B 6/4233; A61B 6/4241; A61B 6/4429; G01N 23/046
    USPC .................................................. 250/370.09
    See application file for complete search history.

(56) References Cited

U.S. PATENT DOCUMENTS

2019/0099150 A1*   4/2019   Konkle et al. ........... A61B 6/00

* cited by examiner

*Primary Examiner* — David P Porta
*Assistant Examiner* — Gisselle M Gutierrez
(74) *Attorney, Agent, or Firm* — McCoy Russell LLP (57) ABSTRACT

Various methods and systems are provided for an imaging detector array. In one example, a detector module of the array has an X-ray sensor assembly coupled to an upper surface of a conductive block and at least one integrated circuit positioned in a recess of the conductive block below the X-ray sensor assembly. The detector module may further include a radiation blocker positioned between the X-ray sensor assembly and the at least one integrated circuit.

20 Claims, 8 Drawing Sheets

METHODS AND SYSTEMS FOR A LAYERED IMAGING DETECTOR

FIELD

Embodiments of the subject matter disclosed herein relate to non-invasive diagnostic imaging and non-destructive testing, and more particularly to computed tomography (CT) detectors and methods for uniform heat distribution across CT detectors.

BACKGROUND

Non-invasive imaging technologies allow images of the internal structures of a patient or an object to be obtained without performing an invasive procedure on the patient or object. In particular, technologies such as computed tomography (CT) use various physical principles, such as the differential transmission of x-rays through the target volume, to acquire image data and to construct tomographic images (e.g., three-dimensional representations of the interior of the human body or of other imaged structures).

Non-attenuated x-rays passing through the target volume may be collected by a CT detector. The CT detector may include an array of detector modules configured to emit light upon interaction with the x-rays. The emitted light may be converted into an electrical signal and used to generate the tomographic images. The detector modules may each be an individual electrical circuit coupled to a common computing device. Digital reconstruction may occur at the computing device, based on the signals received from the array of detector modules.

BRIEF DESCRIPTION

In one embodiment, an imaging system comprises one or more detector modules, each detector module having a plurality of layers, including, an X-ray sensor assembly oriented perpendicular to a vertical axis of the detector module and positioned above a conductive block, a radiation blocker positioned between the X-ray sensor assembly and the conductive block, the radiation blocker configured to block penetration of radiation into the conductive block, and at least one integrated circuit positioned along a side of the conductive block and configured to be shielded from irradiation by the radiation blocker. In this way, degradation of the integrated resulting from exposure to radiation is mitigated, increasing a lifetime and performance of the detector modules.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below:

FIGS. 3-12 are shown approximately to scale.

DETAILED DESCRIPTION

Figure 3:
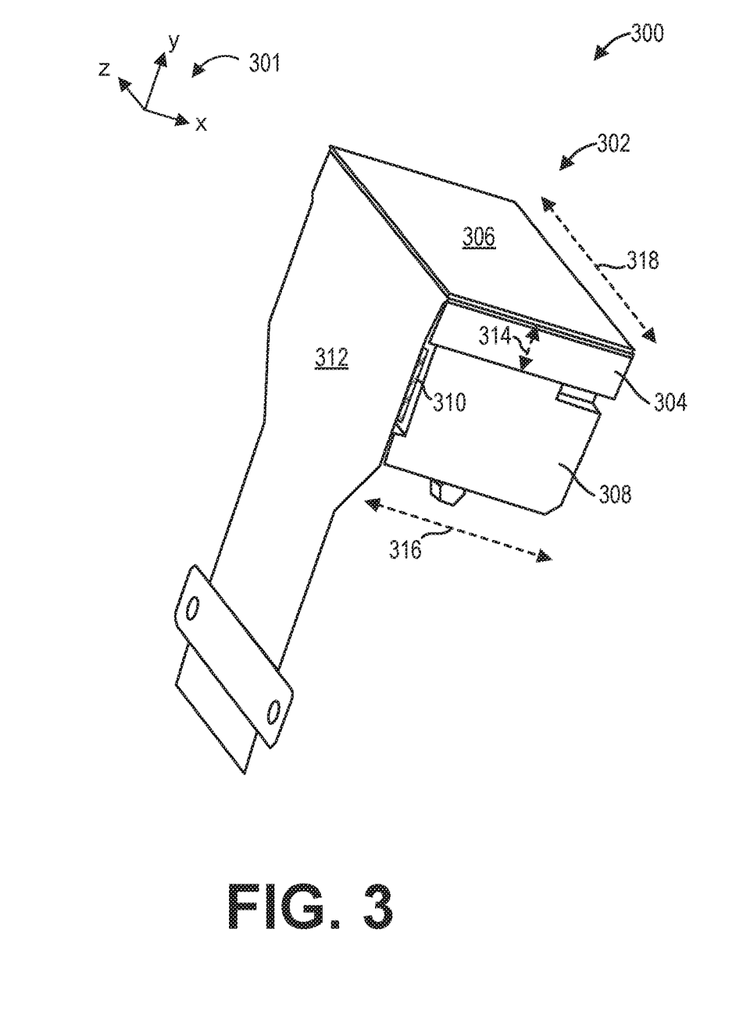
FIG. 3 shows a first example of a detector module coupled to a flex cable from a first view, according to an embodiment.
Figure 4:
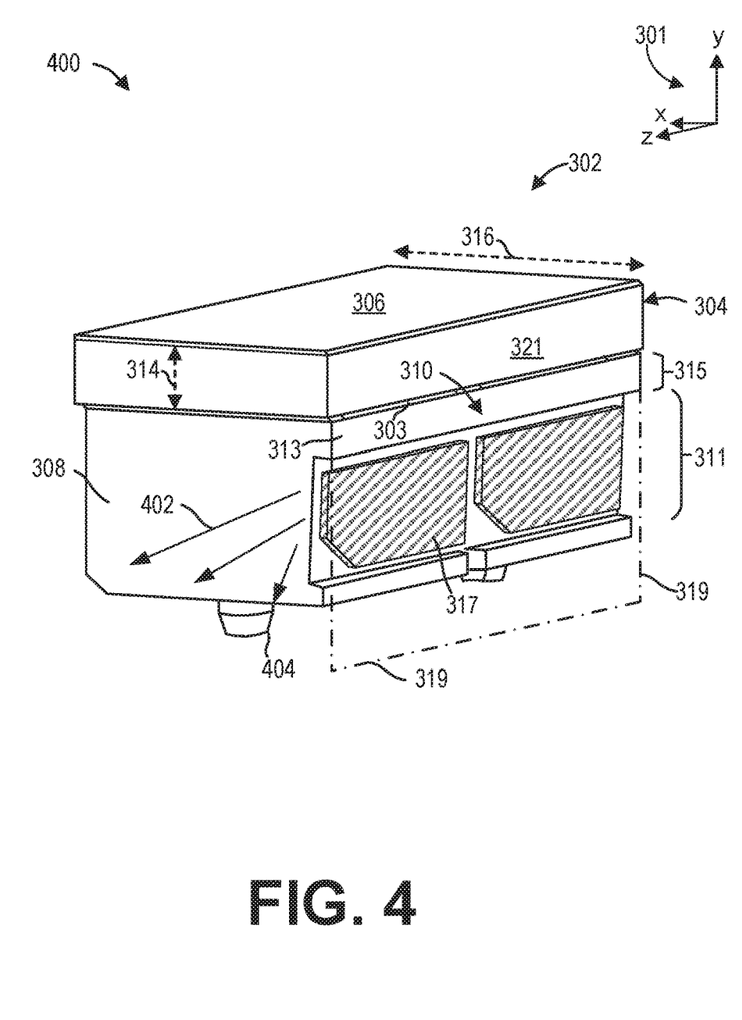
FIG. 4 shows the detector module of FIG. 3 from a second view, without the flex cable.
Figures 5, 6:
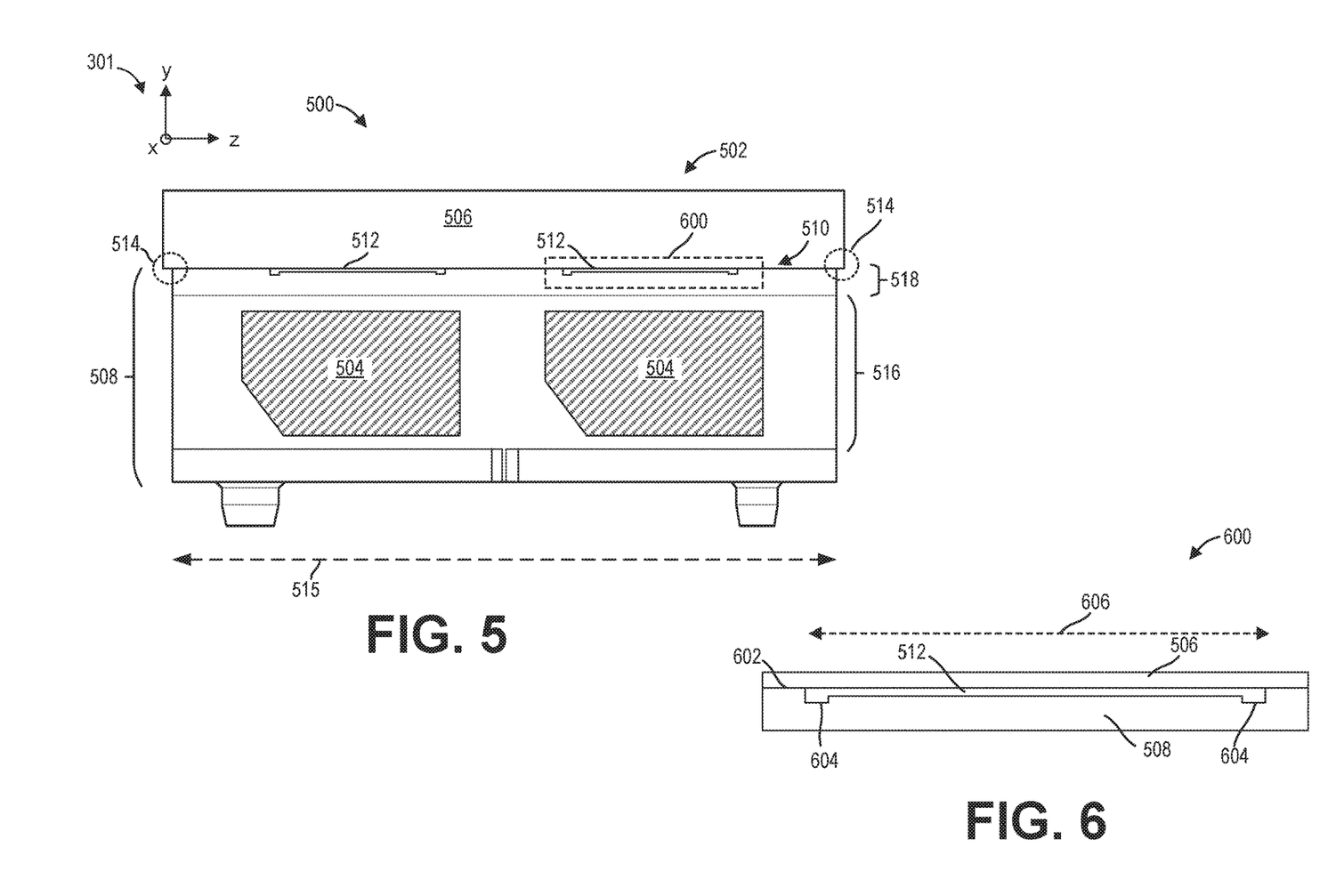
FIG. 5 shows a second example of a detector module adapted with a thermally insulating layer, according to an embodiment.
FIG. 6 shows an expanded view of a section of the detector module of FIG. 5.
Figure 7:
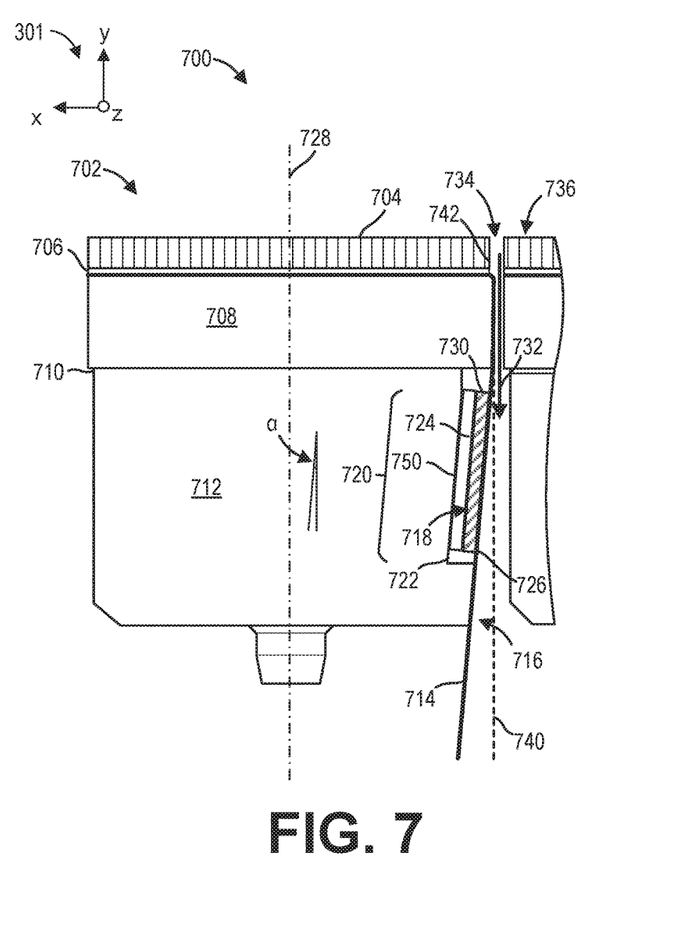
FIG. 7 shows a third example of a detector module, according to an embodiment.
Figure 8:
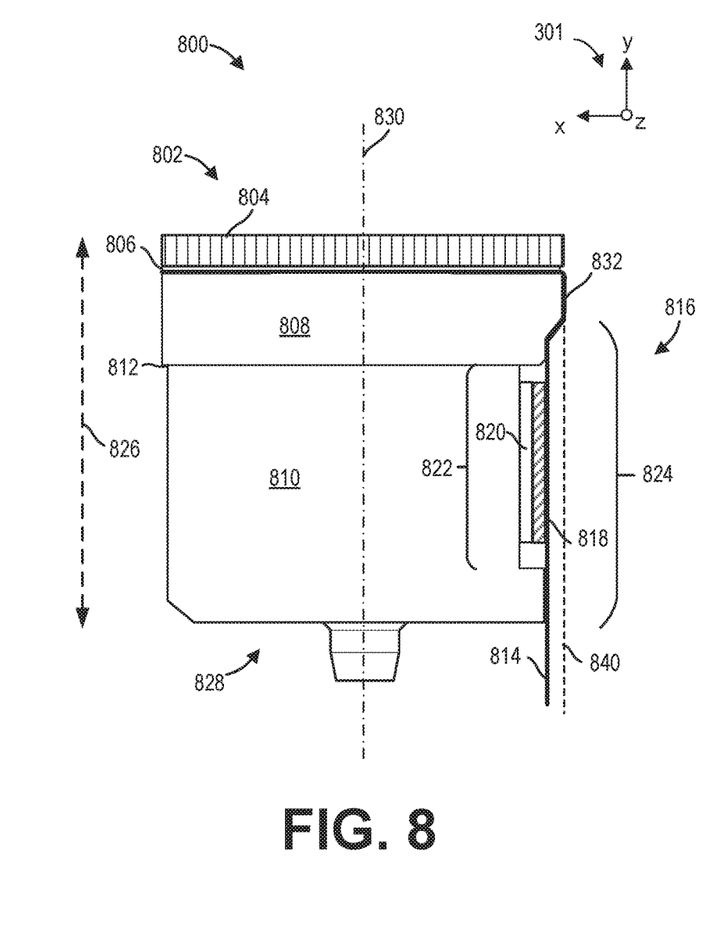
FIG. 8 shows a fourth example of a detector module, according to an embodiment.
Figure 9A:
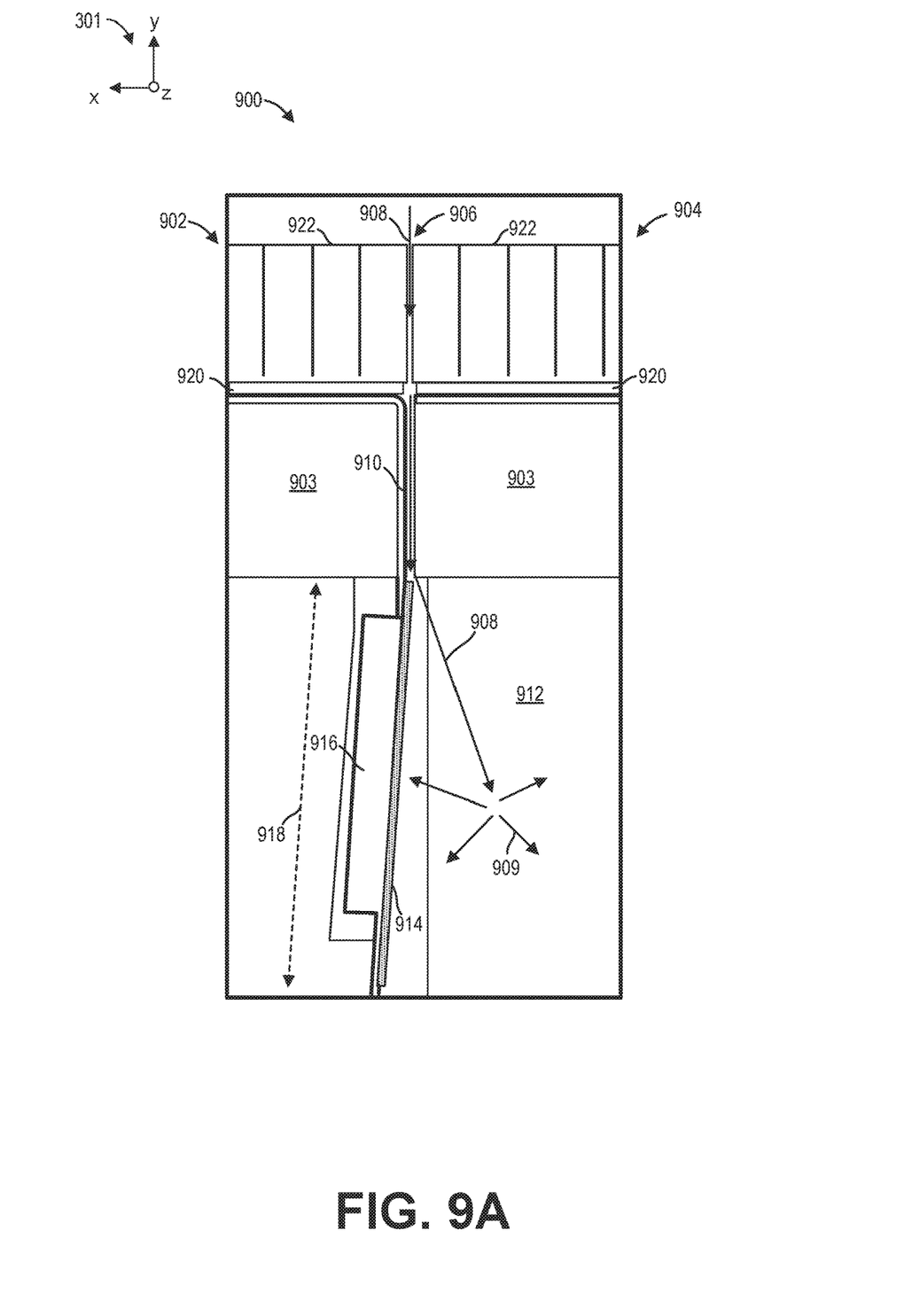
FIG. 9A shows a fifth example of a detector module configured to block scattered radiation using a radiation shield, according to an embodiment.
Figure 9B:
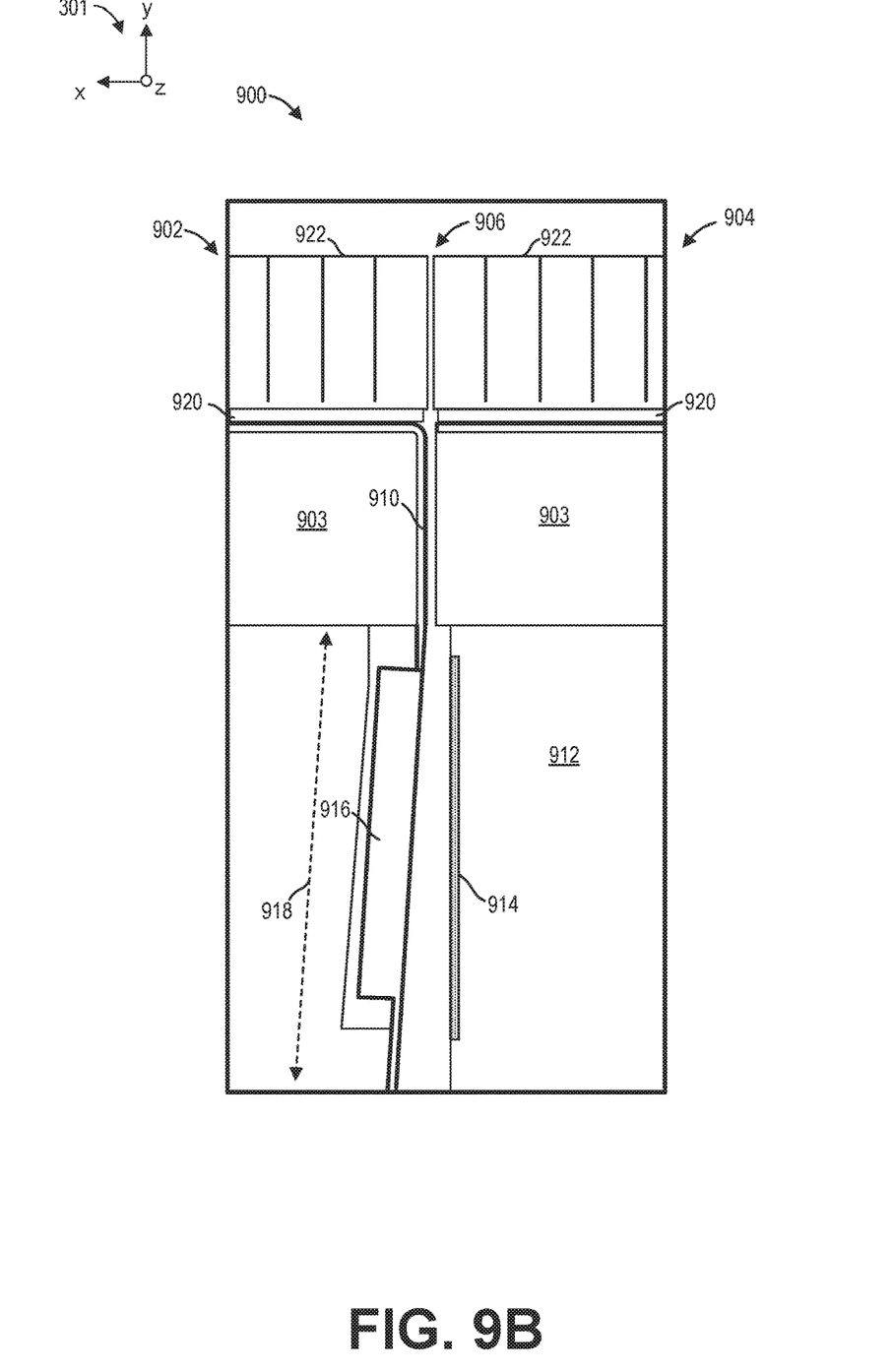
FIG. 9B shows the detector module of FIG. 9A with the radiation shield positioned in an alternate location.
Figure 10:
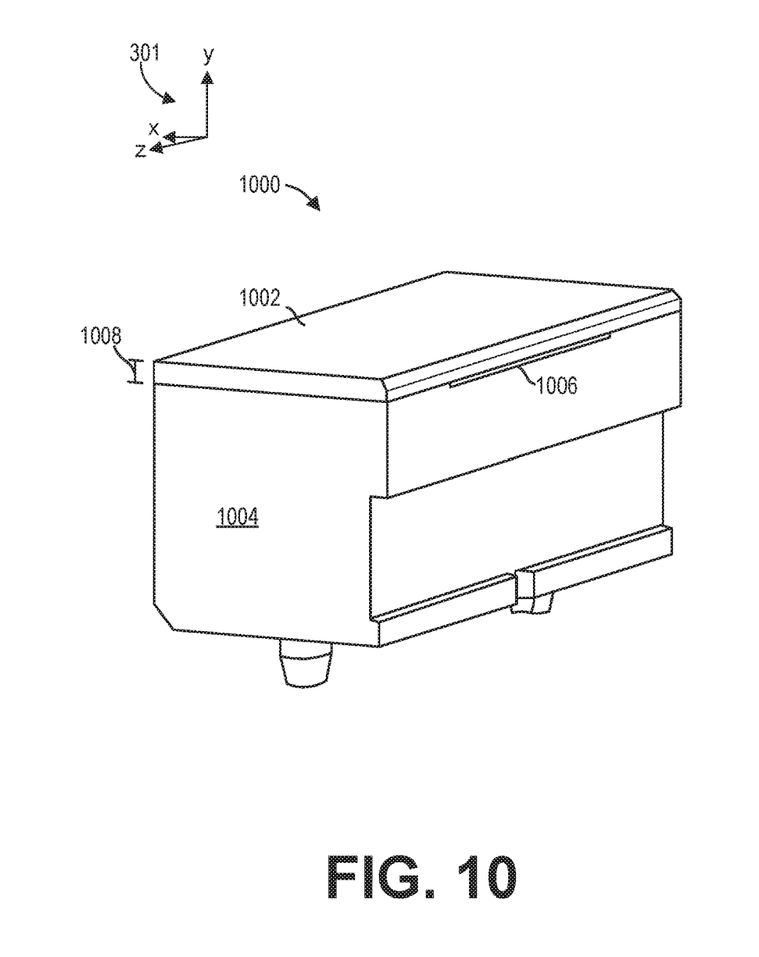
FIG. 10 shows a first alternate example of a conductive block of a detector module, according to an embodiment.
Figure 11:
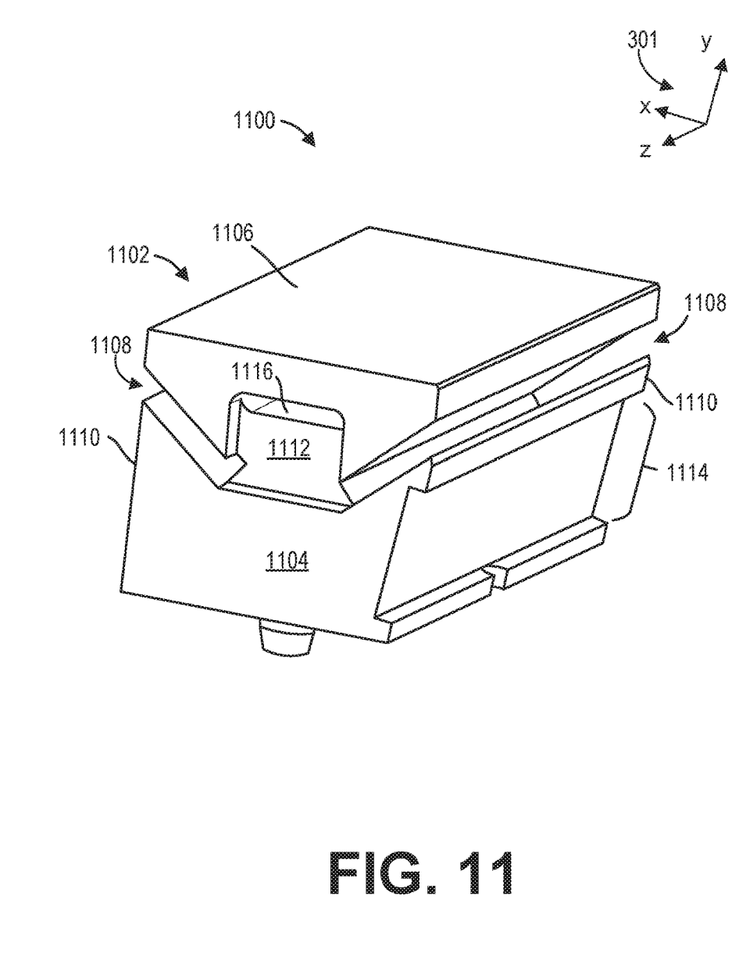
FIG. 11 shows a second alternate example of a conductive block of a detector module, according to an embodiment.
Figure 12:
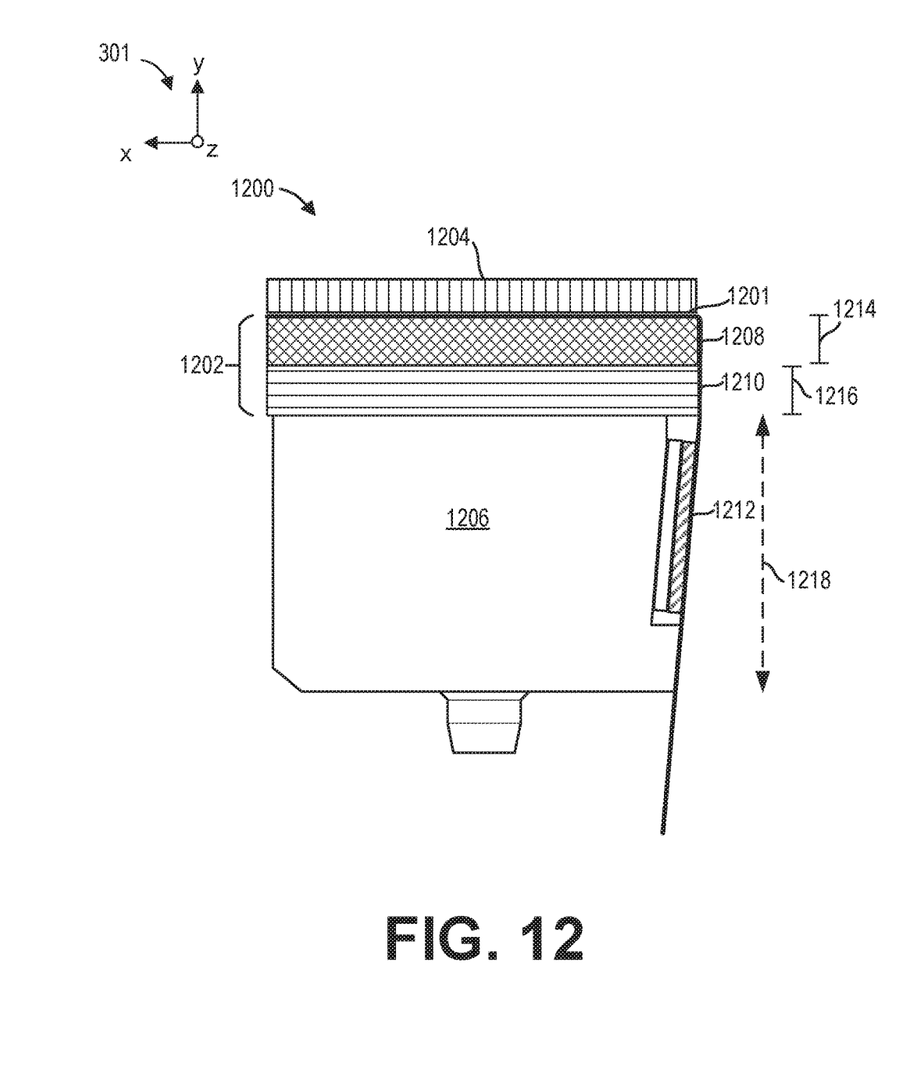
FIG. 12 shows a sixth example of a detector module adapted with a multi-layered radiation blocker, according to an embodiment.

The following description relates to various embodiments of a CT detector. The CT detector may be included in an imaging system, such as an imaging system illustrated in a pictorial view and as a schematic diagram in FIGS. 1 and 2. A plurality of detector modules may form the CT detector, each detector module including at least one application-specific integrated circuit (ASIC), one or more photodiodes, and at least one conductive block. The detector module may further include a radiation blocking layer, e.g., a radiation blocker, and a thermally insulating layer to shield exposure of an ASIC to radiation and to mitigate undesirable heating of a photodiode arranged above the ASIC. An example of a detector module adapted with the radiation blocker and a first type of thermally insulating layer is shown in FIGS. 3 and 4. An example of an alternative thermally insulating layer is depicted in FIG. 5 and an expanded view of the thermally insulating layer is shown in FIG. 6. Additional examples of the detector module with different structural variations to shield the ASIC from radiation are illustrated in FIGS. 7 and 8. As shown in FIGS. 9A and 9B, the detector module may be further adapted with an optional radiation blocker to further shield the ASIC from scattered radiation. Variations in a material and configuration of a conductive block of the detector module are illustrated in FIGS. 10 and 11. An example of a multi-layered radiation blocker is illustrated in FIG. 12.

CT imaging may be used to obtain 3-dimensional (3D) x-ray images where the images may be generated by combining x-ray measurements taken from different angles. The x-ray measurements produce cross-sectional images of a target imaging region which may be digitally stacked to form the 3D image. Images produced by CT imaging may provide more detailed information than conventional, two-dimensional x-ray imaging.

A CT scanner may include a motorized x-ray source configured to rotate around a patient, emitting x-ray beams from an x-ray source that pass through the patient. X-ray beams that are not attenuated by the patient are received at a detector positioned opposite of the x-ray source. The detector may be formed of an array of detector modules, each module including X-ray sensor assemblies such as photodiodes, configured to convert light to electrical signals, or direct conversion detectors, configured to convert x-rays directly to electrical signals. The electrical signal may be transmitted to a circuit board by an ASIC coupled to the detector module. During collection and transmission of the signals, the ASIC may generate heat, leading to a rise in temperature of the detector module. Exposure of the photodiodes to elevated temperature may lead to degradation of the photodiodes and poor and/or inconsistent performance of the detector.

Furthermore, while the ASIC may be positioned below the photodiodes, away from direct irradiation by the x-ray beams, penetration and scattering of the beams may nonetheless expose the ASIC to radiation. Electronic components of the ASIC may be sensitive to radiation and prone to degradation upon exposure. Thus, configuring the detector module with systems to thermally insulate the photodiodes and shield the ASIC from radiation may increase the performance and lifetime of the detector.

The inventors herein have recognized these issues. In one example, the issues described above may be at least partially addressed by a layered detector module adapted with a thermally insulating layer and an x-ray radiation blocking layer. The thermally insulating layer may impede conduction of heat from an integrated circuit of the detector module to one or more photodiodes while the radiation blocking layer may obstruct penetration of x-ray beams, thereby reducing exposure of the integrated circuit. The detector module may be further configured with optional structural variations to enhance x-ray beam attenuation and increase thermal and radiation shielding of the photodiodes and integrated circuit, respectively. Details of the systems and methods for the layered detector module are provided below with reference to FIGS. 3-12.

Figure 1:
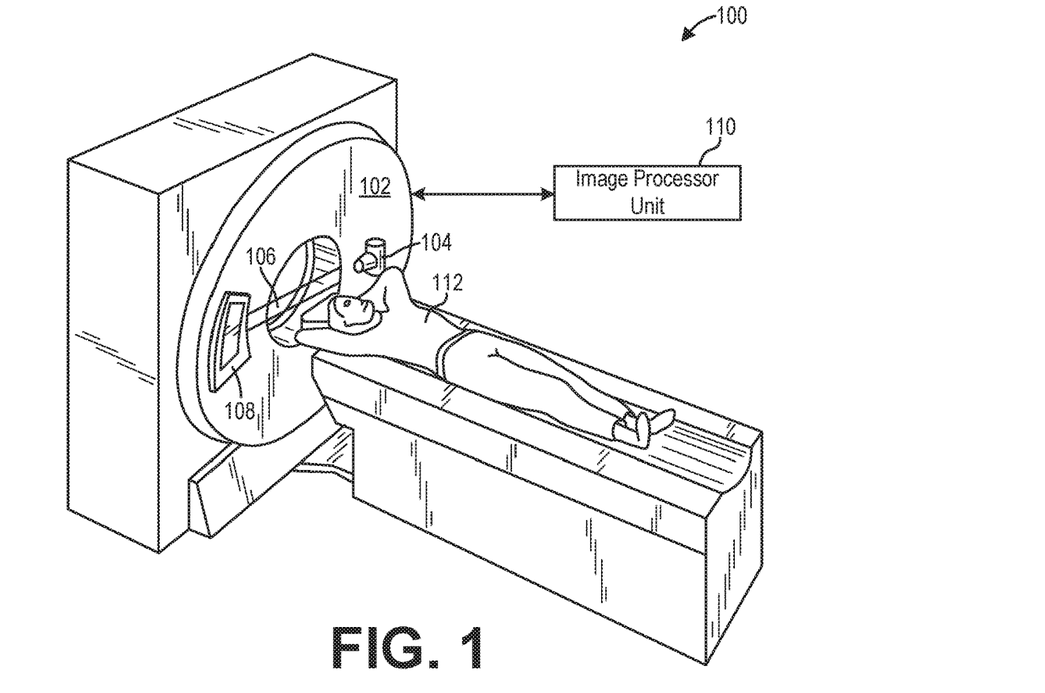
FIG. 1 shows a pictorial view of an imaging system, according to an embodiment.

Turning now to FIG. 1, an exemplary CT system 100 configured for CT imaging is depicted. Particularly, the CT system 100 is configured to image a subject 112 such as a patient, an inanimate object, one or more manufactured parts, and/or foreign objects such as dental implants, stents, and/or contrast agents present within the body. In one embodiment, the CT system 100 includes a gantry 102, which in turn, may further include at least one x-ray source 104 configured to project a beam of x-ray radiation 106 for use in imaging the subject 112. Specifically, the x-ray source 104 is configured to project the x-rays 106 towards a detector array 108 positioned on the opposite side of the gantry 102. Although FIG. 1 depicts only a single x-ray source 104, in certain embodiments, multiple x-ray radiation sources and detectors may be employed to project a plurality of x-rays 106 for acquiring projection data at different energy levels corresponding to the patient. In some embodiments, the x-ray source 104 may enable dual-energy gemstone spectral imaging (GSI) by rapid peak kilovoltage (kVp) switching. In some embodiments, the x-ray detector employed is a photon-counting detector which is capable of differentiating x-ray photons of different energies. In other embodiments, two sets of x-ray tube-detectors are used to generate dual-energy projections, with one set at low-kVp and the other at high-kVp. It should thus be appreciated that the methods described herein may be implemented with single energy acquisition techniques as well as dual energy acquisition techniques.

In some CT imaging system configurations, a radiation source projects a cone-shaped beam which is collimated to lie within an X-Y-Z plane of a Cartesian coordinate system and generally referred to as an "imaging plane." The radiation beam passes through an object being imaged, such as the patient or subject 112. The beam, after being attenuated by the object, impinges upon an array of radiation detectors. The intensity of the attenuated radiation beam received at the detector array is dependent upon the attenuation of a radiation beam by the object. Each detector element of the array produces a separate electrical signal that is a measurement of the beam attenuation at the detector location. The attenuation measurements from all the detector elements are acquired separately to produce a transmission profile.

In some CT systems, the radiation source and the detector array are rotated with a gantry within the imaging plane and around the object to be imaged such that an angle at which the radiation beam intersects the object constantly changes. A group of radiation attenuation measurements, e.g., projection data, from the detector array at one gantry angle is referred to as a "view." A "scan" of the object includes a set of views made at different gantry angles, or view angles, during one revolution of the radiation source and detector. It is contemplated that the benefits of the methods described herein accrue to medical imaging modalities other than CT, so as used herein the term "view" is not limited to the use as described above with respect to projection data from one gantry angle. The term "view" is used to mean one data acquisition whenever there are multiple data acquisitions from different angles, whether from a CT, positron emission tomography (PET), or single-photon emission CT (SPECT) acquisition, and/or any other modality including modalities yet to be developed as well as combinations thereof in fused embodiments.

In certain embodiments, the CT system 100 further includes an image processor unit 110 configured to reconstruct images of a target volume of the subject 112 using an iterative or analytic image reconstruction method. As used herein, the phrase "reconstructing an image" is not intended to exclude embodiments of the present invention in which data representing an image is generated but a viewable image is not. Therefore, as used herein, the term "image" broadly refers to both viewable images and data representing a viewable image. However, many embodiments generate (or are configured to generate) at least one viewable image.

Figure 2:
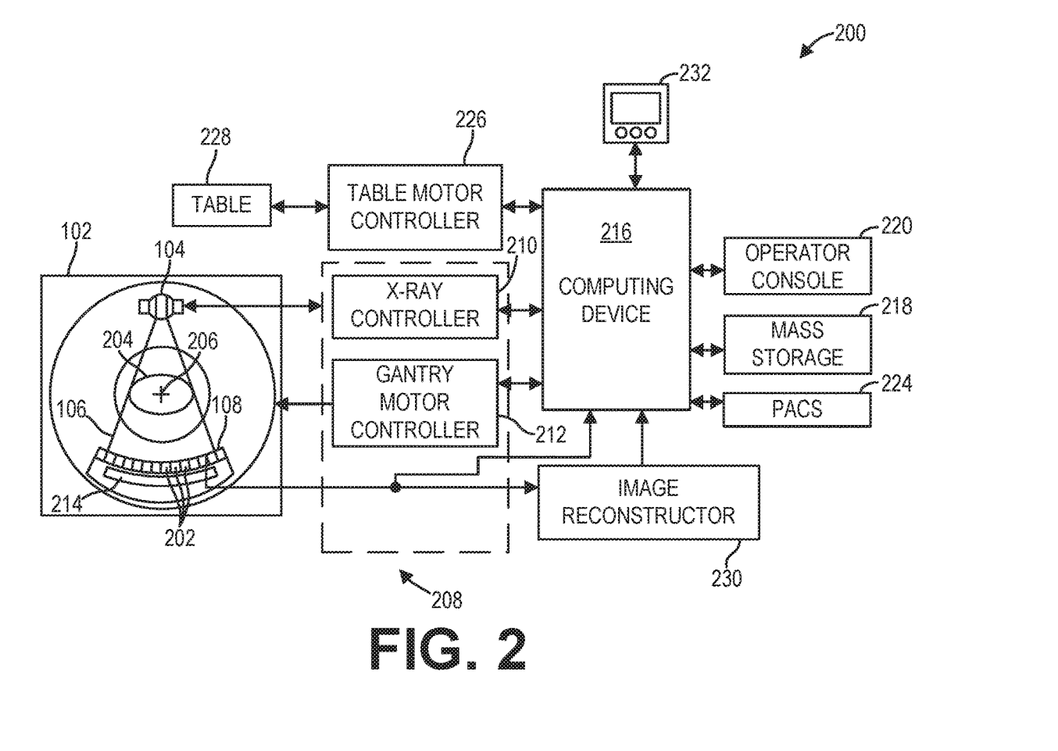
FIG. 2 shows a block schematic diagram of an exemplary imaging system, according to an embodiment.

FIG. 2 illustrates an exemplary imaging system 200 similar to the CT system 100 of FIG. 1. In accordance with aspects of the present disclosure, the imaging system 200 is configured for imaging a subject 204 (e.g., the subject 112 of FIG. 1). In one embodiment, the imaging system 200 includes the detector array 108 (see FIG. 1). The detector array 108 further includes a plurality of detector elements 202 that together sense the x-ray beams 106 (see FIG. 1) that pass through the subject 204 (such as a patient) to acquire corresponding projection data. Accordingly, in one embodiment, the detector array 108 is fabricated in a multi-slice configuration including the plurality of rows of cells or detector elements 202. In such a configuration, one or more additional rows of the detector elements 202 are arranged in a parallel configuration for acquiring the projection data.

In certain embodiments, the imaging system 200 is configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

As the x-ray source 104 and the detector array 108 rotate, the detector array 108 collects data of the attenuated x-ray beams. The data collected by the detector array 108 undergoes pre-processing and calibration to condition the data to represent the line integrals of the attenuation coefficients of the scanned subject 204. The processed data are commonly called projections.

In some examples, the individual detectors or detector elements 202 of the detector array 108 may include photon-counting detectors which register the interactions of individual photons into one or more energy bins. It should be appreciated that the methods described herein may also be implemented with energy-integrating detectors.

The acquired sets of projection data may be used for basis material decomposition (BMD). During BMD, the measured projections are converted to a set of material-density projections. The material-density projections may be reconstructed to form a pair or a set of material-density map or image of each respective basis material, such as bone, soft tissue, and/or contrast agent maps. The density maps or images may be, in turn, associated to form a volume rendering of the basis material, for example, bone, soft tissue, and/or contrast agent, in the imaged volume.

In one embodiment, the imaging system 200 includes a control mechanism 208 to control movement of the components such as rotation of the gantry 102 and the operation of the x-ray source 104. In certain embodiments, the control mechanism 208 further includes an x-ray controller 210 configured to provide power and timing signals to the x-ray source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the detector elements 202 and convert the analog data to digital signals for subsequent processing. The DAS 214 may be further configured to selectively aggregate analog data from a subset of the detector elements 202 into so-called macro-detectors, as described further herein. The data sampled and digitized by the DAS 214 is transmitted to a computer or computing device 216, which may be the image processor unit 110 of FIG. 1. In one example, the computing device 216 stores the data in a storage device or mass storage 218. The storage device 218, for example, may include a hard disk drive, a floppy disk drive, a compact disk-read/write (CD-R/W) drive, a Digital Versatile Disc (DVD) drive, a flash drive, and/or a solid-state storage drive.

Additionally, the computing device 216 provides commands and parameters to one or more of the DAS 214, the x-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) or a touchscreen to allow the operator to specify the commands and/or scanning parameters.

In one embodiment, for example, the imaging system 200 either includes, or is coupled to, a picture archiving and communications system (PACS) 224. In an exemplary implementation, the PACS 224 is further coupled to a remote system such as a radiology department information system, hospital information system, and/or to an internal or external network (not shown) to allow operators at different locations to supply commands and parameters and/or gain access to the image data.

The computing device 216 uses the operator-supplied and/or system-defined commands and parameters to operate a table motor controller 226, which in turn, may control a table 228 which may be a motorized table. Specifically, the table motor controller 226 may move the table 228 for appropriately positioning the subject 204 in the gantry 102 for acquiring projection data corresponding to the target volume of the subject 204. As previously noted, the DAS 214 samples and digitizes the projection data acquired by the detector elements 202. Subsequently, an image reconstructor 230 uses the sampled and digitized x-ray data to perform high-speed reconstruction. In one embodiment, the image reconstructor 230 stores the images reconstructed in the storage device 218. Alternatively, the image reconstructor 230 may transmit the reconstructed images to the computing device 216 for generating useful patient information for diagnosis and evaluation. In certain embodiments, the computing device 216 may transmit the reconstructed images and/or the patient information to a display or display device 232 communicatively coupled to the computing device 216 and/or the image reconstructor 230. In some embodiments, the reconstructed images may be transmitted from the computing device 216 or the image reconstructor 230 to the storage device 218 for short-term or long-term storage.

The various methods and processes described further herein may be stored as executable instructions in non-transitory memory on a computing device (or controller) in imaging system 200. In one embodiment, image reconstructor 230 may include such executable instructions in non-transitory memory, and may apply the methods described herein to reconstruct an image from scanning data. In another embodiment, computing device 216 may include the instructions in non-transitory memory, and may apply the methods described herein, at least in part, to a reconstructed image after receiving the reconstructed image from image reconstructor 230. In yet another embodiment, the methods and processes described herein may be distributed across image reconstructor 230 and computing device 216.

In one embodiment, the display 232 allows the operator to evaluate the imaged anatomy. The display 232 may also allow the operator to select a volume of interest (VOI) and/or request patient information, for example, via a graphical user interface (GUI) for a subsequent scan or processing.

As described above, a detector array may include a plurality of detector elements (e.g., detector 108 and detector elements 202 of FIG. 2). The detector array may be implemented in a variety of imaging systems. Each of the plurality of detector elements may be incorporated into a detector module formed of a number of components such as one or more X-ray sensor assemblies, one or more ASICs, a circuit board, electrical connectors, a heat sink, etc. In examples where the detector array is used in an x-ray imaging system, the X-ray sensor assemblies may be photodiodes or direct conversion detectors. In a computed tomography system, as shown in FIGS. 1 and 2, and described herein, the X-ray sensor assemblies may be photodiodes with scintillators positioned on top of the photodiodes. Heat may be generated at the ASICs during transmission of electrical signals from the photodiodes to the circuit board. Conduction of heat through the detector module may result in undesirable heating of the photodiodes and degrade a performance of the photodiodes. In addition, penetration and scattering of x-ray beams may subject the ASICs to irradiation that may adversely affect transmission of electrical signals.

In order to mitigate exposure of an ASIC to x-ray radiation in a detector module, the detector module may be configured with a layer to block penetration of x-ray beams into the detector module. For example, as shown in FIG. 3 from a first perspective view 300, a first example of a detector module 302 may be equipped with a radiation blocker 304. A set of reference axes 301 are provided for comparison between views, indicating a y-axis, an x-axis, and a z-axis. The radiation blocker 304 may be positioned below a photodiode 306, relative to the y-axis.

The detector module 302 may be a block formed of various layers and components, including the photodiode 306, the radiation blocker 304, a conductive block 308, one or more ASICs 310, and a flex cable 312. The flex cable 312 is coupled to an upper surface, with respect to the y-axis, of the photodiode 306, forming a layer between the photodiode 306 and the radiation blocker, where the photodiode 306 is stacked above the radiation blocker 304. The photodiode 306 may be coupled to the flex cable 312 by a layer of adhesive and the flex cable 312 may be coupled to radiation blocker 304 also by a layer of adhesive.

The radiation blocker 304 is stacked above the conductive block 308 along the y-axis and coupled to the conductive block 308 via a thermally insulating layer 303 (as shown in FIG. 4), the thermally insulating layer 303 described further below. A scintillator, as shown in FIGS. 6 and 7, may be also be included in the detector module 302, the scintillator positioned on top of the photodiode 306 and configured to convert x-ray photons to light. The light may be transmitted to the photodiode 306 which converts light energy into an electrical signal which may be collected by the ASICs 310 and transmitted to a circuit board via the flex cable 312.

A second perspective view 400 of the detector module 302 is illustrated in FIG. 4, depicting the detector module 302 with the flex cable 312 removed. The detector module 302 may include two ASICs 310, as shown in FIG. 4, but may include other quantities of ASICs in other examples, such as one or three. Similarly, other examples may include more than one of the photodiode 306 positioned above the conductive block 308.

The detector module 302 may be further adapted with the thermally insulating layer 303, as shown in FIG. 4, to impede conduction of heat from the ASICs 310 to the photodiode 306. The thermally insulating layer 303 may be disposed between the radiation blocker 304 and the conductive block 308 and implemented so that incorporation of the thermally insulating layer 303 does not include use of any metallic connecting devices, e.g., bolts, screws, etc. The thermally insulating layer is described in further detail below, with reference to FIGS. 5 and 6.

As shown in FIGS. 3 and 4, the photodiode 306 may be a flat, planar layer aligned with the x-z plane. A thickness of the photodiode 306, defined along the y-axis, may be less than a thickness 314 of the radiation blocker 304. The radiation blocker 304 may have a similar width 316 and length 318 as the photodiode 306 and conductive block 308 and may be formed from a material that absorbs energy and/or attenuates x-ray beams. Furthermore, the radiation blocker 304 may include one or more layers of one or more types of material. For example, the radiation blocker 304 may be formed from a high atomic number (e.g., high Z) element, such as molybdenum (Mo), tungsten (W), lead (Pb), tin (Sn) or mixtures and alloys of these metals. A single layer of one type of material may be used, such as one layer of Mo, or multiples layer of one type of material, e.g., more than one layer of Mo or another material, or multiple layers formed of different materials. By locating the radiation blocker 304 directly under the photodiode 306, x-ray beams penetrating through the photodiode 306 may be efficiently absorbed or completely attenuated before the radiation reaches the ASICs 310.

The ASICs 310 may be located in a recess 311 in a side surface 313 at a rear side of the conductive block 308. As such, a plane of rear-facing faces 317 of the ASICs 310 may be oriented at an angle between 0-90 degrees relative to a plane of the photodiode 306, where the photodiode 306 is co-planar with the x-z plane. The recess 311 may be a region along the side surface 313 where the width 316 of the conductive block 308 is reduced. Positioning the ASICs 310 within the recess 311 allows the ASICs 310 to be tucked entirely beneath the radiation blocker 304, with respect to the y-axis. As such, the ASICs 310 do not protrude beyond a rear-facing edge 321 of the radiation blocker 304 along the y-axis, thereby reducing exposure of the ASICs 310 to x-ray photons passing along the side surface 313 of the conductive block 308.

For example, the rear-facing faces 317 of the ASICs 310 do not extend, with respect to the y-axis, beyond an outermost plane 319 of the rear-facing edge 321 of the radiation blocker 304, the outermost plane 319 aligned with the y-z plane. Instead, placing the ASICs 310 in the recess 311 positions the ASICs spaced away from the outermost plane 319. In some examples, the outermost plane 319 of the rear-facing edge 321 of the radiation blocker 304 may also be the outermost plane 319 of a shoulder 315 of the conductive block 308 when the radiation blocker 304 and the conductive block 308 are similar in width 316 and length 318. Furthermore, locating the ASICs 310 in the recess 311 enables detector modules of a detector array to be packaged close together with minimal gaps in between, thereby reducing a footprint of the detector array and promoting reliable and consistent detector performance.

The radiation blocker 304 may be combined with the thermally insulating layer 303 to provide dual shielding effects, e.g., thermal and radiation shielding. The thermally insulating layer 303, as shown in FIG. 4, may be a thin, compared to the radiation blocker 304, layer of an insulating material such as an adhesive or a combination of adhesive and air, e.g., air as an insulating layer with adhesive to attach the radiation blocker 304 to the flex cable 312. The adhesive may be, for example, an epoxy or a curable adhesive. An example of how the thermally insulating layer 303 may be configured is shown in FIG. 5 in a second example of a detector module 502. The detector module 502 is shown in a rear view 500 in FIG. 5, e.g., a side of the detector module 502 to which ASICs 504 are coupled.

The detector module 502 has a radiation blocker 506, which may be the radiation blocker 304 of FIGS. 3 and 4 in one example, arranged on top of a conductive block 508, similar to the conductive block 308 of FIGS. 3 and 4. A thermally insulating layer 510, similar to the thermally insulation layer 303 of FIG. 4, is positioned between the radiation blocker 506 and the conductive block 508, above the ASICs 504. The thermally insulating layer 510 may be one or more slots 512 aligned longitudinally with the x-z plane and co-planar with a photodiode positioned above the radiation blocker 506, e.g., the photodiode 306 of FIGS. 3 and 4. Each of the slots 512 may extend partially through a length 515 of the detector module 502, e.g., along the z-axis, and entirely through a width of the detector module 502, e.g., along the x-axis. However, in other examples, the detector module 502 may have a different number of slots 512 from that shown in FIG. 5 and the slots 512 may instead extend entirely through the length 514 and partially through the width. For example, the detector module 502 may have a single slot that extends entirely across the length 515 and only through a portion of the width of the detector module 502. Other examples may include three or four slots, the slots having same or different lengths, widths and heights (the heights defined along the y-axis).

The slots 512 may be gaps or channels arranged above, with respect to the y-axis, each of the ASICs 504. An expanded view 600 of one of the slots 512, as indicated by a dashed rectangle is shown in FIG. 6. The slot 512 shown in FIG. 6 may be a recess in an upper surface 602 of the conductive block 508. A length 606 of the slot 512 (and a width of the slot, defined along the x-axis) may vary according to a desired bond-line of a thermally non-conductive adhesive applied to the slot 512. When the radiation blocker 506 is coupled to the upper surface 602 of the conductive block 508, the slot 512 is formed, providing an interruption in thermal transmission between the conductive block 508 and the radiation blocker 506. In other words, the adhesive in the slot 512 may be less conductive than a material of the conductive block, thereby impeding transfer of heat from the conductive block 508 upwards into the radiation blocker 506.

As shown in FIG. 6, the slot 512 may include troughs 604 at extreme ends of the slot 512 along the z-axis. The troughs 604 may be regions of the slot 512 where a recess in the upper surface 602 of the conductive block 508 is deepened, resulting in a greater depth, defined along the y-axis, at the troughs 604 than a region of the slot 512 between the troughs 604. The troughs 604 may be configured to receive an overflow of adhesive used to couple the radiation blocker 506 to the conductive block 508. For example, a layer of adhesive may be applied to the upper surface 602 of the conductive block 508 (or to a bottom surface of the radiation blocker 506), between the troughs 604. When the radiation blocker 506 is pressed against the conductive block 508, excess adhesive may seep into the troughs 604, thereby providing reservoirs for adhesive overflow.

Returning to FIG. 5, the radiation blocker 506 may be adapted to provide an overhang 514 where the radiation blocker 506 protrudes, e.g., further outwards along the y-axis, than a surface of a recess 516 in which the ASICs 504 are located, as shown in FIG. 4 by the recess 311 and the rear-facing edge 321 of the radiation blocker 304. The overhang 514 may extend along the x-y plane as well as along the y-z plane. Along the y-z plane, the overhang 514 may protrude along the x-direction beyond a plane of outer surfaces of the ASICs 504, as shown in FIG. 4. The overhang 514 may ensure that the ASICs 504 are maintained entirely under the radiation blocker 506, relative to the y-axis. In some examples, as shown in FIG. 4, the conductive block 508 may have a shoulder 518, similar to the shoulder 315 of FIG. 4, that protrudes along the x-direction by a similar amount as the overhang 514.

By positioning the slots 512 between the radiation blocker 506 and the conductive block 508, undesirable heating of photodiodes of the detector module 502 may be mitigated. For example, returning to FIG. 4, heat generated by the ASICs 310 may be blocked from flowing upwards through the conductive block 308 and into the radiation blocker 304 by the thermally insulating layer 303. As described above, the thermally insulting layer 303 may be a non-conductive adhesive or a combination of adhesive and air. Heat may be force to flow downwards, as indicated by arrows 402, through the conductive block 308 and into a heatsink (not shown) arranged below the conductive block 308. For example, the heatsink may be aligned with the conductive block 308 via alignment pins 404 of the conductive block so that the heatsink is in direct contact with the conductive block 308. The heatsink may be formed of a thermally conductive material that draws heat from the conductive block 308 and into the heatsink.

Positioning of a thermally insulating layer between ASICs and photodiodes of a detector module may reduce conduction of heat to the photodiodes while positioning of a radiation blocker between the photodiodes and the ASICs may alleviate exposure of the ASICs to x-ray irradiation. An orientation of the ASICs within the detector module may further assist in reducing irradiation of the ASICs. Examples of different ASIC configurations are shown in FIGS. 7 and 8.

A second example of a detector module 702 is illustrated in FIG. 7 from a profile view 700, e.g., along the x-y plane. A section of an adjacent detector module 736 is shown to the right of the detector module 702. The detector module 702 includes a scintillator 704 stacked on top of at least one photodiode 706, along the y-axis. Similar to the first example of the detector module 302 of FIGS. 3 and 4, a radiation blocker 708 may be positioned below the photodiode 706, and a conductive block 712 below the photodiode 706 with a thermally insulating layer 710 arranged therebetween. A flex cable 714 is in contact with the photodiode 706, wrapping along a rear side 716 of the detector module 702, and extending downwards to a circuit board (not shown).

The flex cable 714 is coupled to an ASIC 718 positioned along the rear side 716 of the detector module 702. The ASIC 718 is shown substantially aligned with the y-z plane but may be tilted relative to the y-axis by a greater degree in other examples, as described further below. It will be appreciated that herein, description of a component being substantially aligned with an axis refers to an alignment that inclination relative to the axis of up to 10 degrees. The ASIC 718 may be located in a recess 720 in a side surface 722 of the detector module and spaced away from the side surface 722 by a thermal interface 724. The recess 720 may be similar to the recess 311 of FIG. 4. The thermal interface 724 may be in direct contact with both the ASIC 718 and the side surface 722 of the detector module 702, sandwiched in between, and having similar dimensions (such as length, width, and thickness) as the ASIC 718.

The thermal interface 724 may be a pad formed of a thermally conductive material, such as a silicone-based matrix with a ceramic, or a thermally-conductive adhesive (e.g., filled with silver particles). Placement of the thermal interface 724 may facilitate conduction of heat from the ASIC 718 to the conductive block 712, allowing heat generated by the ASIC 718 to be conducted through the conductive block 712 and to a heatsink coupled to the conductive block 712.

The ASIC 718 is positioned entirely under the radiation blocker 708, within the recess 720. The ASIC 718, as well as a surface 750 of the recess 720. may be tilted with respect to the y-axis to reduce a likelihood that radiation penetrating through a small space or gap 734 between the detector module 702 and the adjacent detector module 736, as indicated by arrow 732, does not strike a lower portion of the ASIC 718. For example, the ASIC 718 and the surface 750 of the recess 720 may be inclined by an angle α so that a bottom end 726 of the ASIC 718 (and a bottom end of the recess 720) may be closer to a center line 728 of the detector module 702 and further from an outermost plane 740, described further below, than an upper end 730 of the ASIC 718 (and an upper end of the recess 720). The angle α may be an angle between 5-10 degrees, for example, and may depend on a configuration of components of the detector module 702. In other examples, the angle α may be anywhere between 0-90 degrees. The thermal interface 724 and the side surface 722 of the detector module 702, within the recess 720, may also be included at the angle α.

By tilting the ASIC 718 as shown in FIG. 7, the ASIC 718 is more tucked away under an edge of the radiation blocker 708 than if aligned parallel with the y-axis. For example, the ASIC 718 may be spaced away, towards the center line 728 of the detector module 702, from an outermost plane 740 that defines a furthest protrusion of a rear-facing edge 742 of the radiation blocker 708 along the x-axis. Thus, a likelihood of x-ray beams, passing along the rear side 716 of the detector module 702, irradiating the bottom end 726 of the ASIC 718 is reduced. Adjusting the inclination of the ASIC 718 enables radiation mitigation without inhibiting or adversely affecting the coupling of the ASIC 718 to the side surface 722 of the detector module 702.

It will be appreciated that the conductive block 712 may, in other examples, have a shoulder similar to the shoulder 315 shown in FIG. 4. The shoulder of the conductive block 712 may also protrude along the x-axis to the outermost plane 740. Whether the shoulder of the conductive block is present or not, the upper end 730 of the ASIC 718 may be spaced away from the radiation blocker 708 along the y-axis so that the ASIC 718 does not contact the radiation blocker 708.

Alternatively, instead of tilting an ASIC of a detector module as shown in FIG. 7, the ASIC may be inset further under a radiation blocker. For example, a fourth example of a detector module 802 is shown from a profile view 800 in FIG. 8. The detector module 802 has a scintillator 804 stacked over a photodiode 806. A radiation blocker 808 is positioned below the photodiode 806 and a conductive block 810 is stacked under the radiation blocker 808 with a thermally insulating layer 812 disposed in between. A flex cable 814 extends along a rear side 816 of the detector module 802 and an ASIC 818 is coupled to the flex cable 814 on one side and coupled to a thermal interface 820 on an opposite side of the ASIC 818. The ASIC 818 and the thermal interface 820 are located in a recess 822 in the rear side 816 of the detector module 802.

Along the rear side 816, the detector module 802 has an inset 824 extending along a portion of a height 826 of the detector module 802. For example, the inset 824 may begin at a mid-point along a height of the radiation blocker 808, the height defined along the y-axis, depicted as a cut-out region of the radiation blocker 808, and continuing down the rear side 816 of the radiation blocker 808 to a bottom 828 of the detector module 802. Resulting from a presence of the inset 824, the recess 822 may be shifted closer to a center line 830 of the detector module 802 than the recess 720 of FIG. 7. As such, the ASIC 818 is shifted further away, e.g., closer to the center line 830, from an outermost plane 840, aligned with the y-z plane, defined by protrusion of an outer edge 832 of the radiation blocker 808 along the x-axis. The outer edge 832 provides an overhang that shields the ASIC 818 from x-ray photons penetrating a space between the detector module 802 and an adjacent detector module positioned to the right of the detector module 802 (e.g., the gap 734 of FIG. 7). As a result, the ASIC 818 may be less likely to be exposed to radiation.

In some examples, a detector module may be implemented with both aspects shown in both FIGS. 7 and 8. For example, one or more ASICs may be placed in a recess in a side surface of the detector module and the ASICs may be inclined, as shown in FIG. 7 within the recess. Additionally, the detector module may also have an inset, as shown in FIG. 8 where the tilted ASICs are positioned in the recess which is recessed further into the detector module due to the inset.

A detector module may be further adapted with an additional shielding layer to block scattered x-ray beams. For example, as shown in FIG. 9A in a sectional view 900, a first detector module 902 is positioned adjacent to a second detector module 904, the detector modules separated by a gap 906. The gap 906 may be nominal, e.g., very small compared to widths of the detector modules where the widths are defined along the x-axis, but may still allow x-ray photons to penetrate between first radiation blockers 903 of the first detector module 902 and the second detector module 904, as indicated by arrow 908. The penetrating x-ray photons may be deflected and scattered in any direction by interaction with a material of components of the detector modules, as indicated by arrows 909, such as by a metal forming a conductive block 912 of the second detector module 904.

As an example, a radiation shield 914 may be coupled to surfaces of the flex cable 910 that is facing the second detector module 904. The radiation shield 914 may be a segment of tape formed from a radiation blocking material such as tungsten, copper, lead, or a tungsten-doped coating, etc. By positioning the radiation shield 914 between the ASIC 916 and the second detector module 904, x-ray photons scattered in a direction from the conductive block 912 of the second detector module 904 toward the ASIC 916, as indicated by arrows 909, may be blocked from reaching the ASIC 916.

The radiation shield 914 shown in FIG. 9A may be a non-limiting example of a radiation shield. In other examples, the radiation shield 914 may have a length 918 that extends upwards, into the gap 906, between the conductive blocks 912 of the first and second detector modules 902, 904. For example, the radiation shield 914 may extend up to photodiodes 920 of the detector modules. As another example, as shown in FIG. 9B, the radiation shield 914 may be positioned along a surface of the conductive block 912 of the second detector module 904 proximate to the first detector module 902. In yet another example, the radiation shield 914 may instead be configured as a heavy metal-doped coating on the flex cable 910 or integrated into a material of the flex cable. Alternatively, the gap 906 may be filled with a radiation blocker filler, such as a heavy metal-doped flexible polymer. The filler may be inserted in the gap 906 between scintillators 922 of the first and second detector modules 902, 904, and/or between the photodiodes 920 and the conductive blocks 912 of the detector modules.

Various combinations of the options described above for shielding ASICs from radiation and blocking heat conduction to photodiodes may be implemented in a detector module. For example, the detector module may have a radiation blocker immediately below a photodiode with a thermally insulating adhesive layer positioned between the radiation blocker and a conductive block arranged below the radiation blocker. The detector module may further include a radiation shield coupled to an outwards facing surface of the ASIC. In another example, the detector module may have a thermally insulating adhesive between the radiation blocker and the conductive block, the ASIC may be tilted with respect to a vertical axis of the detector module (as shown in FIG. 7) and include a radiation blocker filler occupying a space between the detector module and an adjacent module. It will be appreciated that numerous combinations have been contemplated without departing from the scope of the present disclosure.

A configuration and composition of a detector module may also be varied to provide radiation blocking properties and modify a fabrication process of the detector module. A first alternative example of a detector module 1000 is illustrated in FIG. 10. The detector module 1000 is shown without a photodiode, ASICs or a flex cable for brevity. The detector module 1000 includes a radiation blocker 1002 layered on top of a conductive block. A thermally insulating layer 1006 may be disposed in an upper surface of the conductive block 1004, configured as at least one slot filled with a thermally non-conductive adhesive.

The radiation blocker 1002 may, in one example, be formed of tungsten which may allow the radiation blocker 1002 to have a reduced thickness 1008. For example, the radiation blocker 304 of the detector module 302 shown in FIGS. 3 and 4 may be formed from molybdenum and the thickness 314 of the radiation blocker 304 may be greater than a thickness 1008 of the radiation blocker 1002 of FIG. 10, when heights of the detector module 302 of FIGS. 3 and 4 and the detector module 1000 of FIG. 10 are equal where the heights are defined along the y-axis.

Tungsten may have a higher x-ray photon absorbing capacity, thus less material is demanded to meet a target minimum threshold of shielding relative to molybdenum. As a result, the detector module 1000 may be lighter than a detector module with a radiation blocker formed of a different material (e.g., molybdenum) and a coefficient of thermal expansion (CTE) of tungsten may be well-matched to a CTE of a detector photodiode which may be formed of silicon. However, the tungsten-based radiation blocker 1002 may not be compatible with thermally insulating adhesives that are used with the molybdenum radiation blocker.

A second alternative example of a detector module 1100 is illustrated in FIG. 11. The detector module 1100 may be formed by over-molding a tungsten-doped polymer cap into an aluminum base 1102 where the detector module 1100 is extruded and machined as a single, continuous unit. For example, a lower portion of the aluminum base 1102 may be a conductive block 1104 of the detector module 1100. An upper portion 1106 may interface with a photodiode, e.g., the photodiode may be coupled to a surface of the upper portion 1106.

The aluminum base 1102 may be fabricated with cavities 1108 extending from sides 1110 of the aluminum base 1102 towards a central region 1112, but not through the central region 1112, of the aluminum base 1102. The tungsten-doped polymer may be over-molded into the cavities 1108 to form a radiation blocker that is divided into three segments. Two of the segments are formed by the filled cavities 1108 and a third segment may be formed by filled a centrally disposed slot 1116 with the tungsten-doped polymer. The slot 1116 may be positioned between the cavities 1108 along the x-axis.

By forming the detector module 1100 as a single over-molded, continuous unit, no adhesive or fasteners are demanded to couple the radiation blocker 1102 to the conductive block 1104. In addition, the detector module 1100 may also be readily scalable to accommodate a variety of detector sizes. However, a CTE of aluminum may differ from a CTE of a silicon-based photodiode and the detector module 1100 may be less structurally stable than a detector module with a molybdenum radiation blocker coupled to a separate conductive base.

Further optional variations in a detector module may include forming a radiation blocker from more than layer of at least two different types of material. For example, as shown in FIG. 12, a detector module 1200 may have a radiation blocker 1202 positioned below both a scintillator 1204 and a photodiode 1201 and above a conductive block 1206, with respect to the y-axis. The radiation blocker 1202 is depicted with a first layer 1208 and a second layer 1210, the first layer 1208 stacked directly over the second layer 1210 but may be spaced away from the second layer 1210 by an adhesive coupling the layers to one another.

The layers of the radiation blocker 1202 may be formed from materials that together provide radiation shielding, thermal resistance, and k-edge emission blocking. Each layer may have different properties. For example, the first layer 1208 may block x-ray photons while the second layer 1210 may hinder thermal conduction from the conductive block 1206 to the photodiode 1201 and also block k-edge emission and back scatter from the first layer 1208. In other examples, the radiation blocker 1202 may be formed of more than two layers, such as three or four layers, and include two or more types of material. Each type of material may have different properties. The more than two layers may include alternating layers of two materials or may each be a different material.

The materials used to form the radiation blocker 1202 may be selected based on, in addition to desired shielding and resistive properties, compatibility with one another and with adjacent components of the radiation blocker 1202. For example, the material(s) of the radiation blocker 1202 may have a CTE similar to a CTE of the photodiode 1201, e.g., similar to a CTE of silicon. In some examples, each layer of the radiation blocker 1202 may be coupled to one or more adjacent layers by adhesive. The adhesive may be a thermally resistive adhesive, e.g., formed of a thermally non-conductive material, such as an adhesive used to form a thermally insulating layer between a radiation blocker and a conductive block of a detector module, as described above. Incorporating one or more layers of the adhesive may further impede transmission of heat from one or more ASICs to the photodiode 1201.

In one example, the first layer 1208 of the radiation blocker 1202 may be formed of tin. Tin may reduce a likelihood of blurring at the photodiode 1201 and block k-edge emission. The second layer 1210 may be formed of lead which may provide effective radiation shielding of at least one ASIC 1212 but may also emit k-edge x-ray photons in multiple directions away from the conductive block 1206, e.g., backscatter. The first layer 1208 may compensate for the k-edge emission at the second layer 1210 by absorbing and/or completely attenuating the emitted photons. In some examples, adding a third layer of tin below the second layer 1210 of lead may be desirable to block any backscatter that is able to penetrate towards the conductive block 1206.

As an example, a first thickness 1214 of the first layer 1208 may be similar to a second thickness 1216 of the second layer 1210, as shown in FIG. 12. However, in other examples, the first thickness 1214 may be greater or less than the second thickness 1216. Additionally an overall thickness, e.g., a sum of the first thickness 1214 and the second thickness 1216, of the radiation blocker 1202 may vary relative to a height 1218 of the conductive block 1206. The first and second thicknesses 1214 and 1216 may be adjusted based on the type of material used. For example, a material with a higher x-ray photon shielding capacity may have a reduced thickness relative to a material that is less effective at blocking x-ray photons. As another example, it may desirable to use a thinner layer when the layer of the radiation blocker 1202 is formed from a heavier material. For example, a thinner layer of lead may be used than of molybdenum.

In this way, a detector for an imaging system may be configured to provide consistent and reliable performance with a prolonged useful life. A detector module of the detector may be adapted with a layered structure to both minimize irradiation of radiation-sensitive integrated circuits and reduce heating of temperature-sensitive photodiodes. A radiation blocker may be implemented in the detector module, beneath the photodiodes, to block penetration of x-ray photons through the photodiodes and further into the detector module. Exposure of the integrated circuits, located in a recess in a side surface of the detector module below the photodiode, to x-ray irradiation may be circumvented by positioning the integrated circuits entirely beneath the radiation blocker. The detector module may also have a thermally insulating layer which may be a layer of thermally resistant adhesive positioned between the photodiodes and the integrated circuits to block heat conduction from the integrated circuits to the photodiodes. The combination of the radiation blocker and the thermally insulating layer may decrease adverse exposure of both the photodiodes and integrated circuits, thereby reducing a demand for replacement or maintenance of the photodiodes and integrated circuits.

A technical effect of configuring the detector module with radiation blocker and the thermally insulating layer is that irradiation of the integrated circuits by x-ray photons are reduced while heating of the photodiodes is inhibited.

FIGS. 1-12 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

In one embodiment, an imaging system includes one or more detector modules, each detector module having a plurality of layers, including, an X-ray sensor assembly oriented perpendicular to a vertical axis of the detector module and positioned above a conductive block, a radiation blocker positioned between the X-ray sensor assembly and the conductive block, the radiation blocker configured to block penetration of radiation into the conductive block, and at least one integrated circuit positioned along a side of the conductive block and configured to be shielded from irradiation by the radiation blocker. In a first example of the system, a thermally insulating layer disposed between the radiation blocker and the conductive block, the thermally insulating layer configured to inhibit conduction of heat from the at least one integrated circuit to the X-ray sensor assembly. A second example of the system optionally includes the first example, and further includes, wherein the thermally insulating layer is a layer of adhesive and wherein the adhesive is at least one of an epoxy and a UV-curable adhesive. A third example of the system optionally includes one or more of the first and second examples, and further includes, wherein the thermally insulating layer is formed of one or more adhesive-filled slots, each slot oriented coplanar with the X-ray sensor assembly and positioned above an integrated circuit of the at least one integrated circuit along the vertical axis of the detector module. A fourth example of the system optionally includes one or more of the first through third examples, and further includes, wherein the one or more adhesive-filled slots are recesses in an upper surface of the conductive block and wherein the one or more adhesive-filled slots have troughs at extreme ends of each slots, the troughs configured to collect excess adhesive coupling the radiation blocker to the conductive block. A fifth example of the system optionally includes one or more of the first through fourth examples, and further includes, wherein the radiation blocker is a layer entirely covering the upper surface of the conductive block and a lower surface of the X-ray sensor assembly and formed of a material that absorbs and/or attenuates x-ray photons. A sixth example of the system optionally includes one or more of the first through fifth examples, and further includes, wherein an edge of the radiation blocker protrudes beyond an outward facing surface of the at least one integrated circuit along a direction perpendicular to the vertical axis and wherein the protrusion of the radiation blocker is configured to provide an overhang to shield the at least one integrated circuit from irradiation. A seventh example of the system optionally includes one or more of the first through sixth examples, and further includes, wherein the outward facing surface of the at least one integrated circuit is spaced away from an outermost plane aligned with the vertical axis and defined by the protrusion of the edge of the radiation blocker. An eighth example of the system optionally includes one or more of the first through seventh examples, and further includes, wherein the at least one integrated circuit is located in a recess along a side of the conductive block and a surface of the recess is tilted with respect to the vertical axis where the tilting positions a bottom end of the recess further away from the outermost plane than an upper end of the recess.

In another embodiment, a detector includes at least one detector module having a layered structure, wherein the layered structure includes, an X-ray sensor assembly, a radiation blocker positioned between the X-ray sensor assembly and a conductive block, configured to block penetration of radiation past the X-ray sensor assembly, one or more integrated circuits positioned along a side of the conductive block, below the X-ray sensor assembly and electrically coupled to the X-ray sensor assembly, and a thermally insulating layer, disposed between the radiation blocker and the conductive block, configured to inhibit heat transmission from the one or more integrated circuits to the X-ray sensor assembly. In a first example of the detector, the one or more integrated circuits are positioned underneath, relative to a vertical axis of the at least one detector module, the radiation blocker and spaced away from an outermost plane aligned with the vertical axis, the outermost plane defined by a protrusion of an edge of the radiation blocker along a direction perpendicular to the vertical axis. A second example of the detector optionally includes the first example, and further includes, wherein the one or more integrated circuits are inclined where a bottom end of each of the one or more integrated circuits is further from the outermost plane of the radiation blocker than an upper end of each of the one or more integrated circuits. A third example of the detector optionally includes one or more of the first and second examples, and further includes, wherein the one or more integrated circuits are aligned parallel with the vertical axis and positioned in an inset extending from a mid-point along a height of the radiation blocker, the height defined along the vertical axis, to a bottom end of the at least one detector module. A fourth example of the detector optionally includes one or more of the first through third examples, and further includes a shield formed of a radiation blocking material and configured to be coupled to at least one of a surface of a cable coupled to the one or more integrated circuits and extending along a side of the conductive block and a surface of an adjacent detector module and wherein the shield is configured to shield the one or more integrated circuits from scattered radiation. A fifth example of the detector optionally includes one or more of the first through fourth examples, and further includes, wherein the shield extends along at least a length of the one or more integrated circuits, the length defined along the vertical axis, and wherein the shield is positioned between the one or more integrated circuits and the adjacent detector module. A sixth example of the detector optionally includes one or more of the first through fifth examples, and further includes a shield formed of a radiation blocking material and coupled to a cable, the cable coupled to the one or more integrated circuits, by at least one of a coating applied to a surface of cable extending at least along a length of the one or more integrated circuits, the length defined along the vertical axis, and incorporation of the radiation blocking material into a material of the cable and wherein the shield is configured to shield the one or more integrated circuits from scattered radiation. A seventh example of the detector optionally includes one or more of the first through sixth examples, and further includes, wherein the radiation blocker includes one or more layers of one or more types of radiation blocking material, the one or more layers stacked along the vertical axis, and wherein at least one of the one or more types of radiation blocking material is configured with at least one of thermally resistant and k-edge emission blocking properties.

In yet another embodiment, a detector module includes a radiation blocker aligned perpendicular to a vertical axis of the detector module and positioned below an X-ray sensor assembly and above a first surface of a conductive block, the first surface also aligned perpendicular to the vertical axis, at least one integrated circuit coupled to a cable and positioned at a second surface of the conductive block, the second surface different from the first surface and substantially aligned with the vertical axis, and a thermally insulating layer coupled to a bottom surface of the radiation blocker and the first surface of the conductive block. In a first example of the detector module, a thermal interfacing pad positioned between the at least one integrated circuit and the second surface of the conductive block, the thermal interfacing pad configured to conduct heat from the at least one integrated circuit to the conductive block. A second example of the detector module optionally includes the first detector module, and further includes a heat sink positioned below the conductive block and configured to draw heat from the at least one integrated circuit through the conductive block away from the X-ray sensor assembly.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. An imaging system, comprising:
    one or more detector modules, each detector module having a plurality of layers, including;
        an X-ray sensor assembly oriented perpendicular to a vertical axis of the detector module and positioned above a conductive block;
        a radiation blocker positioned between the X-ray sensor assembly and the conductive block, the radiation blocker configured to block penetration of radiation into the conductive block; and
        at least one integrated circuit positioned along a side of the conductive block and configured to be shielded from irradiation by the radiation blocker.

2. The imaging system of claim 1, further comprising a thermally insulating layer disposed between the radiation blocker and the conductive block, the thermally insulating layer configured to inhibit conduction of heat from the at least one integrated circuit to the X-ray sensor assembly.

3. The imaging system of claim 2, wherein the thermally insulating layer is a layer of adhesive and wherein the adhesive is at least one of an epoxy and a UV-curable adhesive.

4. The imaging system of claim 2, wherein the thermally insulating layer is formed of one or more adhesive-filled slots, each slot oriented co-planar with the X-ray sensor assembly and positioned above an integrated circuit of the at least one integrated circuit along the vertical axis of the detector module.

5. The imaging system of claim 3, wherein the one or more adhesive-filled slots are recesses in an upper surface of the conductive block and wherein the one or more adhesive-filled slots have troughs at extreme ends of each slots, the troughs configured to collect excess adhesive coupling the radiation blocker to the conductive block.

6. The imaging system of claim 1, wherein the radiation blocker is a layer entirely covering the upper surface of the conductive block and a lower surface of the X-ray sensor assembly and formed of a material that absorbs and/or attenuates x-ray photons.

7. The imaging system of claim 1, wherein an edge of the radiation blocker protrudes beyond an outward facing surface of the at least one integrated circuit along a direction perpendicular to the vertical axis and wherein the protrusion of the radiation blocker is configured to provide an overhang to shield the at least one integrated circuit from irradiation.

8. The imaging system of claim 7, wherein the outward facing surface of the at least one integrated circuit is spaced away from an outermost plane aligned with the vertical axis and defined by the protrusion of the edge of the radiation blocker.

9. The imaging system of claim 8, wherein the at least one integrated circuit is located in a recess along a side of the conductive block and a surface of the recess is tilted with respect to the vertical axis where the tilting positions a bottom end of the recess further away from the outermost plane than an upper end of the recess.

10. A detector for an imaging system, comprising:
at least one detector module having a layered structure, wherein the layered structure includes;
an X-ray sensor assembly;
a radiation blocker positioned between the X-ray sensor assembly and a conductive block, configured to block penetration of radiation past the X-ray sensor assembly;
one or more integrated circuits positioned along a side of the conductive block, below the X-ray sensor assembly and electrically coupled to the X-ray sensor assembly; and
a thermally insulating layer, disposed between the radiation blocker and the conductive block, configured to inhibit heat transmission from the one or more integrated circuits to the X-ray sensor assembly.

11. The detector of claim 10, wherein the one or more integrated circuits are positioned underneath, relative to a vertical axis of the at least one detector module, the radiation blocker and spaced away from an outermost plane aligned with the vertical axis, the outermost plane defined by a protrusion of an edge of the radiation blocker along a direction perpendicular to the vertical axis.

12. The detector of claim 11, wherein the one or more integrated circuits are inclined where a bottom end of each of the one or more integrated circuits is further from the outermost plane of the radiation blocker than an upper end of each of the one or more integrated circuits.

13. The detector of claim 11, wherein the one or more integrated circuits are aligned parallel with the vertical axis and positioned in an inset extending from a mid-point along a height of the radiation blocker, the height defined along the vertical axis, to a bottom end of the at least one detector module.

14. The detector of claim 10, further comprising a shield formed of a radiation blocking material and configured to be coupled to at least one of a surface of a cable coupled to the one or more integrated circuits and extending along a side of the conductive block and a surface of an adjacent detector module and wherein the shield is configured to shield the one or more integrated circuits from scattered radiation.

15. The detector of claim 14, wherein the shield extends along at least a length of the one or more integrated circuits, the length defined along the vertical axis, and wherein the shield is positioned between the one or more integrated circuits and the adjacent detector module.

16. The detector of claim 10, further comprising a shield formed of a radiation blocking material and coupled to a cable, the cable coupled to the one or more integrated circuits, by at least one of a coating applied to a surface of cable extending at least along a length of the one or more integrated circuits, the length defined along the vertical axis, and incorporation of the radiation blocking material into a material of the cable and wherein the shield is configured to shield the one or more integrated circuits from scattered radiation.

17. The detector of claim 10, wherein the radiation blocker includes one or more layers of one or more types of radiation blocking material, the one or more layers stacked along the vertical axis, and wherein at least one of the one or more types of radiation blocking material is configured with at least one of thermally resistant and k-edge emission blocking properties.

18. A detector module, comprising:
a radiation blocker aligned perpendicular to a vertical axis of the detector module and positioned below an X-ray sensor assembly and above a first surface of a conductive block, the first surface also aligned perpendicular to the vertical axis;
at least one integrated circuit coupled to a cable and positioned at a second surface of the conductive block, the second surface different from the first surface and substantially aligned with the vertical axis; and
a thermally insulating layer coupled to a bottom surface of the radiation blocker and the first surface of the conductive block.

19. The detector module of claim 18, further comprising a thermal interfacing pad positioned between the at least one integrated circuit and the second surface of the conductive block, the thermal interfacing pad configured to conduct heat from the at least one integrated circuit to the conductive block.

20. The detector module of claim 18, further comprising a heat sink positioned below the conductive block and configured to draw heat from the at least one integrated circuit through the conductive block away from the X-ray sensor assembly.

* * * * *